United States Patent
Savran et al.

(10) Patent No.: US 9,494,557 B2
(45) Date of Patent: *Nov. 15, 2016

(54) MICRO-FLUIDIC SYSTEM USING MICRO-APERTURES FOR HIGH THROUGHPUT DETECTION OF CELLS

(75) Inventors: Cagri A. Savran, West Lafayette, IN (US);
(Continued)

(73) Assignee: Purdue Research Foundation, West Lafayette, IN (US)

( * ) Notice: Subject to any disclaimer, the term of this patent is extended or adjusted under 35 U.S.C. 154(b) by 41 days.

This patent is subject to a terminal disclaimer.

(21) Appl. No.: 14/001,963

(22) PCT Filed: Apr. 5, 2012

(86) PCT No.: PCT/US2012/032356
§ 371 (c)(1),
(2), (4) Date: Oct. 8, 2013

(87) PCT Pub. No.: WO2012/138882
PCT Pub. Date: Oct. 11, 2012

(65) Prior Publication Data
US 2014/0024049 A1    Jan. 23, 2014

Related U.S. Application Data

(60) Provisional application No. 61/471,762, filed on Apr. 5, 2011.

(51) Int. Cl.
*G01N 33/553* (2006.01)
*G01N 27/74* (2006.01)
(Continued)

(52) U.S. Cl.
CPC ......... *G01N 27/745* (2013.01); *B01L 3/50273* (2013.01); *B01L 3/502761* (2013.01);
(Continued)

(58) Field of Classification Search
None
See application file for complete search history.

(56) References Cited

U.S. PATENT DOCUMENTS

| | | | |
|---|---|---|---|
| 6,676,904 B1 * | 1/2004 | Lee | G01N 33/537 |
| | | | 422/186.1 |
| 7,828,948 B1 * | 11/2010 | Hatch | B01D 57/02 |
| | | | 204/455 |

(Continued)

FOREIGN PATENT DOCUMENTS

| | | |
|---|---|---|
| DE | 10116938 C1 | 11/2002 |
| WO | 2010091304 A1 | 8/2010 |

OTHER PUBLICATIONS

Chronis, Nikolas, et al "A Microfabricated Bio-Magnetic Separator Based on Continuous Hydrodynamic Parallel Flow,"Micro Total Analysis Systems 2001, Kluwer Academic Publishers, NL, (2201-01-01) pp. 497-498.

(Continued)

*Primary Examiner* — Eric B Crawford
(74) *Attorney, Agent, or Firm* — Fish & Richardson P.C.

(57) ABSTRACT

A microfluidic detection system for micrometer-sized entities, such as biological cells, includes a detector component incorporating a plate with a plurality of opening, the plate separating two chambers, one in communication with a fluid source containing target cells bound to magnetic beads. The openings are sized to always permit passage of the magnetic beads therethrough into a lower one of the chambers and are further sized to always prevent passage of the target cells from the upper one of the chambers. The detector component further includes a magnet positioned to pull unbound magnetic beads through the openings and to capture target cells bound to magnetic beads on the surface of the plate. The microfluidic detection system includes a pump flowing (Continued)

the fluid through the detector component at high flow rates of milliliters per minute for high throughput detection of target cells.

24 Claims, 4 Drawing Sheets

(75) Inventors: Chung-Li Chang, West Lafayette, IN (US); Philip S. Low, West Lafayette, IN (US)

(51) Int. Cl.
*G01N 33/543* (2006.01)
*B01L 3/00* (2006.01)
*G01N 33/574* (2006.01)
*G01N 1/40* (2006.01)

(52) U.S. Cl.
CPC ...... *G01N 33/54326* (2013.01); *G01N 33/574* (2013.01); *B01L 2200/0652* (2013.01); *B01L 2200/0668* (2013.01); *B01L 2300/0877* (2013.01); *B01L 2400/043* (2013.01); *G01N 2001/4016* (2013.01)

(56) References Cited

U.S. PATENT DOCUMENTS

| | | |
|---|---|---|
| 2003/0134416 A1 | 7/2003 | Yamanishi et al. |
| 2004/0084370 A1* | 5/2004 | Singh ............... B01D 61/28 210/645 |
| 2005/0148064 A1* | 7/2005 | Yamakawa ....... B01L 3/502761 435/287.2 |
| 2007/0025883 A1 | 2/2007 | Tai et al. |
| 2007/0190653 A1* | 8/2007 | Heinrich ............ G01N 33/5002 435/345 |
| 2007/0207548 A1 | 9/2007 | Blankenstein |
| 2008/0160537 A1 | 7/2008 | Luotola et al. |
| 2008/0318203 A1 | 12/2008 | Tran et al. |
| 2008/0318324 A1 | 12/2008 | Chiu et al. |
| 2009/0305901 A1 | 12/2009 | Seemann et al. |
| 2010/0068764 A1* | 3/2010 | Sista ................. B01L 3/502761 435/79 |
| 2010/0123457 A1 | 5/2010 | Shinoda |
| 2010/0233822 A1 | 9/2010 | Prins et al. |
| 2010/0248345 A1* | 9/2010 | Luxton ................... B01L 99/00 435/287.1 |
| 2010/0315628 A1* | 12/2010 | Mertsching ........ G01N 15/1463 356/301 |

OTHER PUBLICATIONS

Pourima, B. et al., "Immuno-Magnetic Separation Followed by Solid-Phase Cytometry for the Rapid Detection and Enumeration of Pathogens in Surface Water," European Cells and Materials vol. 3 Suppl. 2, 2002 (pp. 45-47).

Chung, Yao-Kuang et al. "An Electrical Biosensor for the Detection of Circulating Tumor Cells," Biosensors and Bioelectronics 26 (2011) pp. 2520-2526.

European Search Report correspondence to European application No. 12768609.5 dates Jul. 28, 2014, (11 pages).

International Search Report and Written Opinion corresponding to international application No. PCT/US2012/032356 date mailed Oct. 24, 2012 (8 pages).

Office Action; U.S. Appl. No. 14/037,476; Dec. 31, 2015; 25 pp.

* cited by examiner

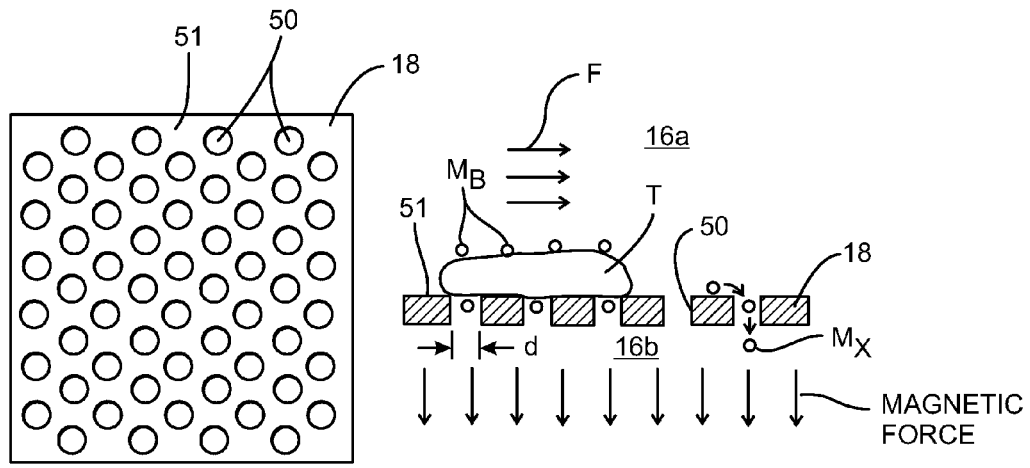
FIG. 3
FIG. 4
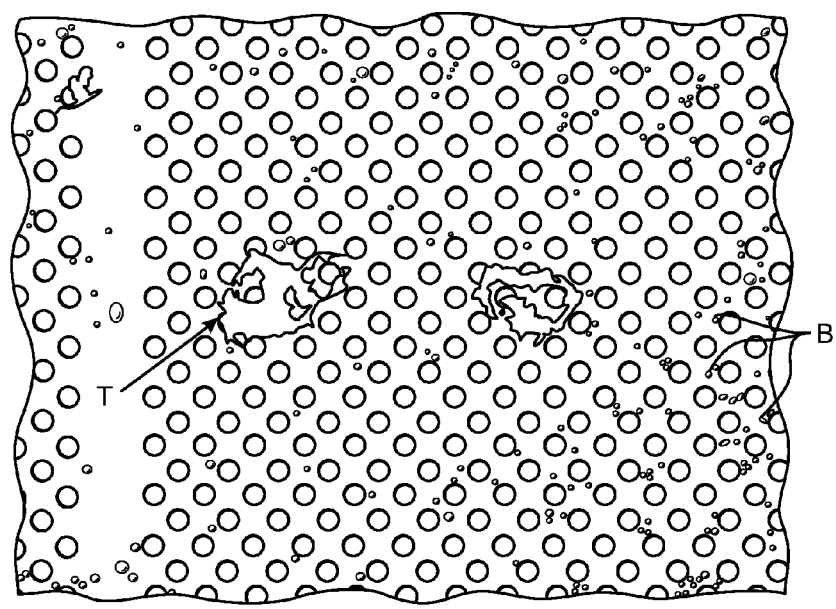
FIG. 6

MICRO-FLUIDIC SYSTEM USING MICRO-APERTURES FOR HIGH THROUGHPUT DETECTION OF CELLS

PRIORITY CLAIM

The present application is a non-provisional application claiming priority to provisional application Ser. No. 61/471,762, filed on Apr. 5, 2011, in the name of the same inventors, the entire disclosure of which is incorporated herein by reference.

TECHNICAL FIELD

The present invention generally relates to microfluidics and particularly to detecting targeted cells present in sample fluids.

BACKGROUND

Circulating tumor cells (or CTCs) are rare cells present in the blood of metastatic cancer patients. Quantitative detection of CTCs is important for early detection of cancer as well as monitoring of the disease progression and response to therapy. CTC count correlates with overall tumor burden and can often serve as more reliable indicators of metastatic disease than molecular disease markers. For example, the level of prostate specific antigen (PSA) can often rise due to benign prostate hyperplasia (common in people over 60) and hence may not necessarily indicate cancer.

The presence of a significant number of CTCs can be a reliable indicator of the presence of cancer. Also, possible recurrence after surgery can be detected much earlier by CTCs than by most molecular markers. Another advantage is that CTCs can be further interrogated after detection; sequencing of the genome and transcriptome could reveal the mutations that had led to cancer as well as the expression levels of the genes in question. The cells can also be cultured, grown and tested with different combinations of chemotherapeutic agents for drug discovery and personalized medicine.

Detecting CTCs however is a challenging task because of their scarcity in blood samples, as few as single cell in multiple milliliter (mL) blood samples. The current favored approach to detecting whole cells in clinical and laboratory settings is flow cytometry, wherein labeled cells are detected as they flow in single file through an optical detector. This technology is used widely from vaccine analysis to monitoring of AIDS. However, the high cost and large size of flow cytometers usually limits this testing approach to central facilities shared by many users. Furthermore, since the cells have to pass through a sensing portion of the flow cytometers in a single file manner, volumetric sample throughput is relatively low and cytometers need to run for long times to analyze large samples. For so-called "rare" cells—i.e., cells that are scarce in a fluid sample, such as CTC cells—relatively large volume samples may be required to find the cells. In this instance, the current flow cytometers can be prohibitively expensive for frequent diagnostic usage.

Microfluidic cell detectors have been developed to overcome the cost and size limitations of traditional flow cytometers in certain applications. These sophisticated systems can successfully interrogate small samples, on the order of $\mu Ls$ (microliters), but such systems have been found to have limited capability for analyzing large samples, on the order of multiple mLs. Most microfluidic systems offer good performance in analyzing small, microliter- or nanoliter-sized sample volumes. However, because of their micrometer dimensions, microfluidic "lab-on-a-chip" detectors need many hours to process large, milliliter-sized sample volumes. Slow flow rates in microfluidic assays are usually a consequence of the microscale dimensions of the sensing channels. These dimensions are necessary to increase the probability of a rare cell (i.e., a CTC) binding on the walls of the microchannels and in some cases to increase the signal-to-noise ratio of the underlying detection mechanism. Thus, the prior microfluidic cell detectors can be generally inefficient and can require prohibitively long analysis times for analyzing the large volume samples necessary for the detection of rare targets like CTCs.

In one microfluidic detection system developed by the Toner and Haber groups of Massachusetts General Hospital, a lab-on-a-chip is populated with antibody-functionalized 100 $\mu m$ diameter posts spaced 50 $\mu m$ apart to create fluid flow paths. In another chip design, the posts were replaced with a herringbone structure to actively assist mixing of the cells and increase their probability to bind the functionalized walls. In these studies, flow rates used with clinical samples were on the order of 1 mL per hour, at which rate processing a typical 7.5 mL blood sample could take many hours. In order to reduce the fluidic transport times to a manageable level of minutes rather than hours, the flow rate through these prior systems would have to be increased by one or two orders of magnitude. In general the necessary modifications to prior microfluidic systems can be problematic because: 1) the fluidic resistance of the micron-sized flow channels and the associated macro-to-micro connections would be very high; 2) a high flow rate through a small cross-sectional area would result in a high "linear speed" which would create shear stresses beyond levels that could be sustained by the antibody/cell binding on the device wall and lead to detachment of the cells; and 3) too high a linear speed would detrimentally affect the capture efficiency of the target cells in the first place. Increasing the size of the channels would allow higher flow rates but this would significantly reduce the probability of the target cells' interaction with the functionalized walls.

In the case of other microfluidic devices that use electronic detection techniques, larger dimensions would reduce the device's detection sensitivity since most microdevices need some form of focusing of targets onto a small sensor area for detection. Other researchers have parallelized their microfluidic detectors (many micro-channels side by side) to overcome the throughput problem. However, the flow rates that are used can be on the order of only 10 microliters ($\mu Ls$) per minute, which can lead to hours of time to process the large volume samples necessary for CTC detection.

A high-throughput yet relatively simple and robust rare cell detection system would be highly beneficial in many research and clinical settings. Therefore, a sensor apparatus is needed that can detect rare cells, such as CTCs, in whole blood in a high-throughput manner by which sample fluids at rates of milliliters per minute (as opposed to microliters per minute) are processed to capture the contained cells. Such a system would also be highly useful in detecting various other types of cells, bacteria and spores present in sample fluids or in the environment.

SUMMARY

According to one aspect of the current teachings a fluidic system including a detector component with micro-apertures is disclosed which is configured to detect target cells bound by recognition elements, such as magnetic beads, in a high-throughput analysis for flow rates of milliliters per minute. In particular, a microfluidic detection system is provided for detection of target cells in a fluid containing a quantity of magnetic beads and a quantity of target cells bound to one or more magnetic beads, in which each target cell bound to a magnetic bead has a smallest effective dimension greater than a smallest effective dimension of each magnetic bead. In one aspect, the system comprises a detector component including a body defining a reservoir and a sensor chip in the form of an apertured plate disposed within the reservoir and separating the reservoir into a first chamber and a second chamber. The plate includes a plurality of micro-openings, each opening having smallest effective dimension greater than the smallest effective dimension of each magnetic bead and less than the smallest effective dimension of each target cell bound to a magnetic bead. In one aspect, the first chamber of the reservoir has a first inlet and a first outlet, in which the first inlet is fluidly connectable to a source of the fluid containing the target cells, while the first outlet is fluidly connectable to a collection vessel.

The detector component further includes a magnet disposed relative to the reservoir so that the second chamber of the reservoir and the apertured plate are situated between the magnet and the first chamber of the reservoir. The magnet configured to generate a magnetic force sufficient to attract magnetic beads in the first chamber of the reservoir to the second chamber of the reservoir. The microfluidic detection system further comprises a pump for continuously flowing the fluid from the source of the fluid containing the target cells through the first chamber of the reservoir.

A method is provided for detecting target cells in a fluid containing a quantity of magnetic beads and a quantity of target cells bound to one or more magnetic beads, in which each target cell bound to a magnetic bead has a smallest effective dimension greater than largest effective dimension of each magnetic bead. In one aspect, the method comprises: continuously flowing the fluid through a first chamber of a reservoir separated from a second chamber of the reservoir by an apertured plate, each opening in the plate having a smallest effective dimension greater than the smallest effective dimension of each magnetic bead and less than the smallest effective dimension of each target cell bound to a magnetic bead; and applying a magnetic force beneath the apertured plate sufficient to draw magnetic beads not bound to a target cell through the apertures into the second chamber and sufficient to hold the target cells bound to one or more magnetic beads against the surface of the apertured plate within the first chamber of the reservoir.

BRIEF DESCRIPTION OF DRAWINGS

FIG. 3 is a plan view of a sensor chip micro-perforated plate for use in the system shown in FIG. 1A.

FIG. 4 is a side representation of the operation of the sensor chip shown in FIG. 3 to capture target cells and extract unbound magnetic recognition elements.

FIG. 6 is a bright-field microscopic picture of target cells captured on a sensor chip in accordance with a disclosed embodiment.

DETAILED DESCRIPTION

Figure 1A:
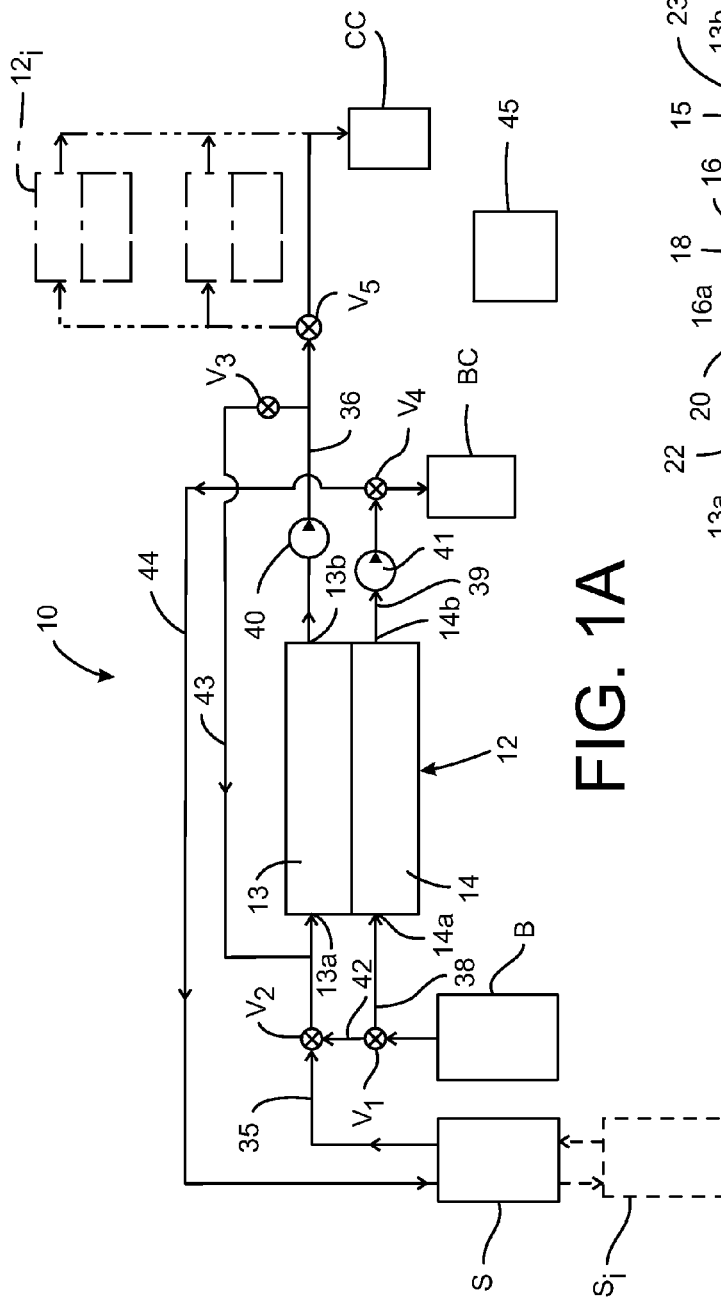
FIG. 1A is a schematic view of a microfluidic detection system according to the present disclosure.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one of ordinary skill in the art to which this invention pertains.

The present disclosure provides a micro-fluidic system with a detector component having an apertured plate or chip configured to provide high-throughput analysis of mLs (milliliters) per minute of a fluid sample flowing through relatively large (millimeter (mm) as opposed to micrometer ($\mu$m)) flow channels. The fluid sample may be a bodily fluid, including but not limited to whole blood, processed blood, serum, plasma, saliva and urine, or environmental fluids, including but not limited to fluid samples from rivers, sewage lines, water processing facilities and factories. Using functionalized beads capable of binding to target cells in three dimensions, the system eliminates the need for chemical affinity-based binding of the cells to a stationary two-dimensional chip surface. The system uses both convective fluid flow to assist in mass transport of target cells bound by functionalized magnetic beads, and magnetic sieving of the bound cells onto a plate or chip with micro-apertures which captures the cells but allows free magnetic beads (i.e., those not bound to target cells) to pass through the apertures. In certain embodiments the magnetic beads simultaneously serve to: 1) affinity-based bind specific target cells; 2) magnetically transport the bound cells to the plate or chip surface; and 3) generate recognition or labeling signals for detection. The novel fluidic system of the present disclosure can analyze large amounts of sample fluids, including clinically significant amounts of bodily fluids such as whole blood, in a relatively short amount of time.

FIG. 1A depicts a schematic of a micro-fluidic system 10 according to one embodiment of the present disclosure. The system 10 includes a detector component 12 having a first flow segment 13 and a parallel second flow segment 14. The first flow segment 13 is provided with an inlet 13a and an outlet 13b, in which the inlet is connected by an inlet conduit 35 to a sample fluid source S. The outlet 13b is connected by outlet conduit 36 to a collection vessel CC, which is suitable for collecting and storing target cells isolated by the microfluidic detection system 10. The second inlet 14a is connected by an inlet conduit 38 to a source of a buffered or physiologically inert or non-reactive solution B. The second outlet 14b is connected by an outlet conduit 39 to a collection vessel BC for collecting buffered solution exiting the detector component 12.

Figure 1B:
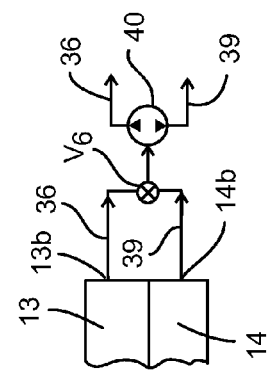
FIG. 1B is a schematic view of a portion of the system shown in FIG. 1B modified in accordance with an alternative embodiment.

In one embodiment a pump 40 is provided for flowing fluid from the sample source S through the first flow segment 13 of the detector component 12. In the embodiment shown in FIG. 1 the pump 40 is integrated into the outlet conduit 36 to draw fluid through the detector component. However, it is contemplated that the pump 40 may be situated within the inlet conduit 35 as desired. The embodiment of FIG. 1A further includes a second pump 41 that is integrated into the outlet conduit 14b to flow the buffer fluid from source B through the second flow segment 14 of the detector component 12. The pump 41 may be provided in the inlet conduit 38 to draw buffer fluid from the source B and pump it through the second flow segment 14. Alternatively the same pump, such as pump 40, may be used to pump both the sample fluid from the source S through the first flow segment 13 and the fluid from source B through the second flow segment 14, as depicted in the enlarged segment shown in FIG. 1B. In this embodiment the two outlet conduits 36, 39 are connected to the pump 40 through a bi-directional valve V6 that is controllable to selectably connect one or the other outlet for flow through the pump, according to a fluid flow protocol discussed herein.

Returning to FIG. 1A, the microfluidic system 10 incorporates bypass lines that are selectively activated according to a fluid flow protocol described below. A bypass line 42 is provided between the buffer source B and the inlet conduit 35 to the first flow segment 13 of the detector component. A valve V1 is operable to control flow of buffer solution from the source B into both inlet conduits 35, 38, while a valve V2 is operable to control flow of buffer solution into the first inlet conduit 35.

In a second bypass path, a bypass line 43 is connected between the first outlet conduit 36 and the first inlet conduit 35. This bypass line thus returns fluid exiting the first flow segment 13 of the detector component back to the inlet 13a for the first flow segment. A valve V3 controls fluid flow through the second bypass line 43. A third bypass path includes the bypass line 44 from the second outlet conduit 39 to the source S containing the sample fluid. A valve V4 is configured to direct the flow of buffer fluid exiting the second flow segment 14 either to the buffer collection vessel BC or to the third bypass line 44. The system 10 is provided with a control module 45 that is operable to control the pump(s) 40 (and 41 if present) as well as the valves to control the flow of fluids through each flow segment 13, 14 of the detector component 12, according to a flow protocol described herein.

The microfluidic system 10 may be configured to accept sample fluids from multiple sources $S_i$. The multiple sources $S_i$ may be connected in series or in parallel, with appropriate valving to connect the particular source to the inlet conduit 35 to the first flow segment 13 of the detector component. The system may be further modified to include additional detector components $12i$ connected to the outlet conduit 36 from the first flow segment 13, by way of a control valve V5.

Figure 2:
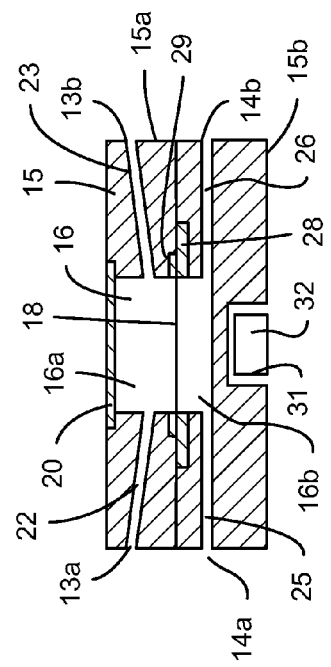
FIG. 2 is a side cross-sectional view of a detector component according to the present disclosure for use in the detection system shown in FIG. 1.

The flow of sample fluid and buffer solution through the system 10, and particularly through the detector component 12, has thus far been described. Details of the detector component 12 and its function are illustrated in FIGS. 2-4. Turning first to the cross-sectional view in FIG. 2, the detector component 12 includes a body 15 that may be in the form of two halves 15a, 15b that are combined to form the complete component. The body 15 defines a reservoir 16 that is separated into a first chamber 16a and a second chamber 16b by a sensor chip in the form of a micro-apertured plate 18. The first chamber 16a is in communication with the first flow inlet 13a and the first flow outlet 13b and thus forms the first flow segment 13 of the detector component. A first inlet channel 22 communicates between the first chamber 16a and the inlet 13a, while a first outlet channel 23 communicates with the outlet 13b. In the illustrated embodiment, the two channels are angled toward the reservoir 16, or defined at a non-planar angle relative to the reservoir, so that the target cells and sample fluid do not accumulate within the channel 22 or inlet conduit 35.

The second chamber 16b is in communication with the respective second inlet and outlet 14a, 14b to form the second flow segment 14 of the detector component. An inlet channel 25 communicates between the second chamber and the second inlet 14a, which an outlet channel 26 communicates with the second outlet 14b. The two channels 25, 26 can be angled but need not be since the second chamber 16b is connected to the buffer solution source B and no target cells flow through this second fluid flow path 14.

The reservoir 16 may be open at one side of the detector component 12, with the reservoir opening sealed and closed by a window or viewing panel 20. The viewing panel 20 is oriented to provide an unobstructed view of the apertured plate 18 within the reservoir 16. In one embodiment the viewing panel 20 is optically transparent to permit direct visualization of the surface of the apertured plate.

The sensor chip or apertured plate 18 may be supported by a plate mounting 28, formed around the perimeter of the plate, that is trapped between the two body halves 15a, 15b when they are coupled together. A seal 29 may be provided on one or both sides of the plate mounting 28 to ensure a fluid-tight seal between the two chambers 16a, 16b. Details of the apertured plate are shown in FIGS. 3-4. In particular, the plate 18 includes an upper surface 51 and a plurality of micro-sized apertures or openings 50 defined therethrough. In one embodiment the openings are generally uniformly sized and have a largest effective dimension d that is less than the smallest effective dimension of a target cell T (FIG. 4) that is to be detected. Moreover, the smallest effective dimension d of the plate openings is greater than a largest effective dimension of magnetic recognition elements M. For the purposes of the present disclosure, the term "effective dimension" refers to a dimension of a particular element measured along a particular axis. For a circular opening in the plate or a spherical magnetic bead, the smallest and largest effective dimensions are the same and are simply the diameter of the opening or bead. For an oblong opening, the largest effective dimension is the length of the opening along its long axis, while the smallest effective dimension is the width along the short axis. The target cells may not exhibit a uniform three-dimensional shape, (such as a sphere) so the cell will have a different dimension depending upon the axis of measurement. For cells of this type, the term "smallest effective dimension" refers to the smallest of those measurements. Thus, the relative effective dimensions of the plate openings are such that a magnetic bead can always pass through any opening no matter how the bead is oriented, while a target cell can never pass through any opening regardless of how it is oriented.

The microfluidic system 10 is configured to detect and isolate target cells T that are bound to recognition elements M. Thus, the fluid source S holds a sample fluid that contains target cells, for instance a blood sample of a patient that contains circulating tumor cells (CTCs) or a sample that has exemplary tumor cell lines such as lymph node carcinoma of the prostate cells (LNCaP) or ovarian cancer cells (IGROV). The fluid sample further contains recognition elements in the form of magnetic beads M that bind to the target cells. Details of the target cells and recognition elements will follow, but with respect to the openings 50 in plate 18 it can be appreciated that the size of the openings is calibrated so that any free magnetic beads M (i.e., beads that have not bound to a target cell T) will pass freely through the opening, such as the beads $M_X$ on the right side of the plate in FIG. 4. On the other hand, the openings 50 are sized so that the target cells T cannot pass therethrough, with or without any magnetic beads bound thereto, such as beads $M_B$.

The significance of the magnetic beads M can be appreciated by referring back to FIG. 2. In particular, the body 15 of the detector component 12 includes a magnet 32 mounted within a cavity 31 beneath the second chamber 16b. In particular, the magnet 32 is positioned so that the magnetic force attracts magnetic beads M within the first chamber 16a toward the apertured plate 18. It is this magnetic force that pulls the free magnetic beads $M_X$ through the openings 50, as illustrated in FIG. 4, even while the beads are under the influence of a fluid flow F that is substantially parallel to the surface 51 of the plate 18. This same magnetic force also attracts beads $M_B$ that are bound to a target cell T, which are also under the influence of the parallel fluid flow F. However, since the target cell T is too large to pass through any opening the magnetic force serves to hold the bound target cell against the surface 51 of the apertured plate 18. In certain instances the target cell T is large enough relative to the magnetic beads M to have several beads $M_B$ bound to the cell. As depicted in FIG. 4, some of the bound beads $M_B$ extend partially into an opening 50. The beads $M_B$ are held within the opening by the magnetic force, which not only holds the bound target cell T to the plate surface 51 but also restrains or "locks" the cell against translating along the surface or being washed away under the influence of the fluid flow F. Thus, the bound beads $M_B$ not only capture target cells but also help prevent the captured target cells from bunching up or collecting at the outlet end of the first chamber 16a.

The magnet 32 is calibrated relative to the magnetic beads M to exert a magnetic force sufficient to pull the beads toward the apertured plate but not so strong as to break the bound beads $M_B$ away from a target cell T captured on the plate surface 51. The magnetic force is also sufficiently strong to pull the beads and target cells out of the fluid flow F that tends to propel the beads and cells in a flow path parallel to the surface 51 of the sensor chip plate 18. In a specific example the magnet is a NdFeB Cube Magnet (about 5×5×5 mm) with a measured flux density and gradient of 0.4 T and 100 T/m, respectively. Other magnets are envisioned including but not limited to larger or smaller permanent magnets made of various materials, and electromagnets that are commercially available or manufactured using standard or microfabrication procedures and that are capable of generating time-varying magnetic fields. In the illustrated embodiment of FIG. 2 the magnet 32 is housed within a cavity 31 formed in the bottom half 15b of the housing. However, the magnet may be affixed to or supported relative to the outside of the detector component 12 provided that it is oriented in a manner to draw the magnetic beads M from the first chamber 16a to the second chamber 16b. It is further contemplated that the magnet 32 may be associated with the detector body 15 so that the distance of the magnet from the apertured plate 18 may be varied to thereby vary the magnetic force applied to the magnetic beads in the first chamber 16a. The magnetic force may thus be calibrated to a particular magnetic bead. In addition, the magnet 32 may be moved to remove the magnetic force entirely according to a flow protocol for the microfluidic system 10. Removal of the magnetic field can facilitate the removal of captured target cells from the plate surface so that the target cells may be transported or flushed to a separate collection vessel CC.

In another embodiment, a magnetic field may be applied from the top of the detector component 12 or directly above the surface 51 of the sensor chip plate 18. This magnetic field may thus "levitate" the captured target cells off the surface 51 to further facilitate their removal. It is contemplated in this embodiment that the magnetic field of the magnet 32 is disrupted as described above so that the magnetic field applied from the top of the component does not "compete" with the original capturing magnetic field.

Figure 5A:
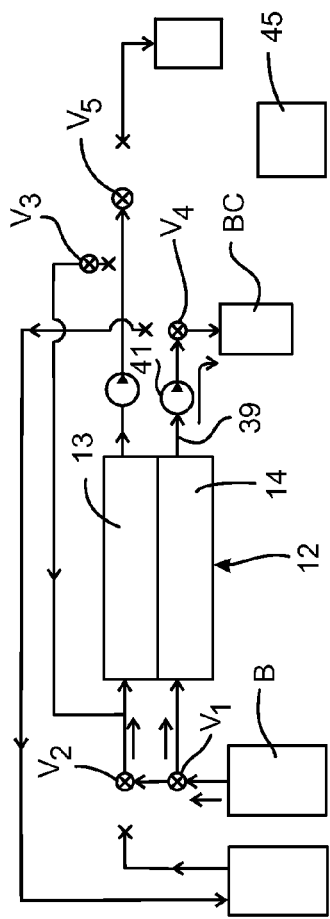
FIGS. 5A-D are schematic views of the microfluidic detection system of FIG. 1A, showing fluid flow paths in different stages of operation of the system.

As explained above, the pump(s) 40 (41) and the valves V1-V5 are controlled according to a flow protocol adapted to; a) prepare the detector component 12 to receive a fluid containing bound target cells; b) capture the bound target cells; c) flush unbound magnetic beads; and d) extract captured target cells. In a first step of the protocol, the system is primed with an non-reactive or buffered solution from source B. The solution from source B is preferably non-reactive to the target cells T, to the recognition elements or magnetic beads B, and to any ligands, antibodies, aptamers, peptides, low molecular weight ligands, or antigens used to functionalize and bind the recognition elements. In a specific embodiment the solution may be a phosphate buffered saline (PBS). Referring to FIGS. 1A and 5A, the reservoir 16 is initially flooded with PBS by opening valve V1, moving valve V4 to close the bypass line 44 but open the flow path to the collection container BC, and moving valve V2 to close the inlet conduit 35 to the sample source S and open the conduit to the bypass line 42. Valves V3 and V5 are closed so that all of the fluid exiting the detector component 12 is fed to the buffer collection container BC. The buffered solution PBS flows freely through both chambers 16a, 16b and through the apertured plate 18 so that all fluid flows through the second outlet channel 26 and second outlet 14b into outlet conduit 39 and collection container BC. In certain embodiments it may be desirable to open valve V5 to pump PBS from chamber 16a into collection vessel CC in order to avoid any pressure increase within the chamber. The pump 41 is thus activated to control the flow of PBS through both flow segments 13, 14. In the alternative configuration of FIG. 1B, the pump 40 provides the motive force for fluid flow with the valve V6 open to both outlets 13b, 14b but with pump discharge to only the second outlet conduit 39. It can be appreciated that this initial flow of PBS through the system will purge the air from the reservoir and channels.

Figure 5B:
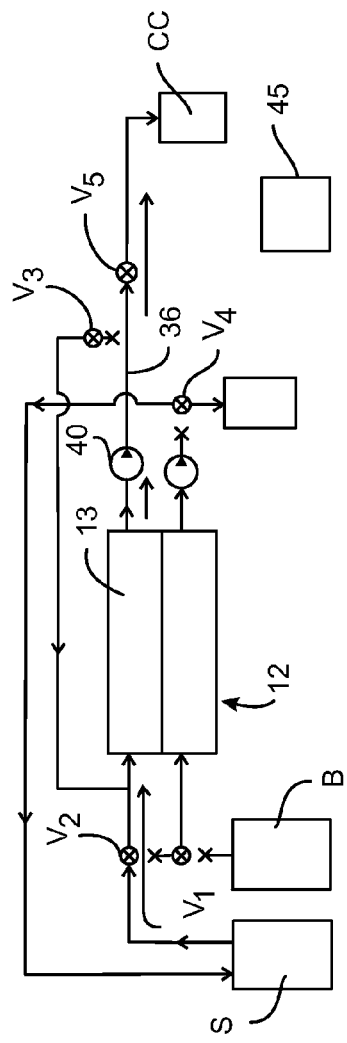

With the detector component primed, the buffered solution fluid circuit is deactivated by closing the valves V1 and V4, closing the bypass line 42 at valve V2, and deactivating pump 41. The first chamber 16a is now ready to receive the sample fluid from source S by opening valve V2 to the inlet conduit 35 and valve V5 to the collection vessel CC, as illustrated in FIG. 5B. Pump 40 is activated to draw the sample fluid from the source S through the detector component 12, and more particularly to pull the sample fluid through the first inlet 13a into the first chamber 16a. The magnet 32 is activated to pull the magnetic beads M to the apertured plate 18, as depicted in FIG. 4. It can be appreciated that the rate of flow F of the sample fluid is calibrated so that the fluid pressure does not overcome the magnetic force. By way of non-limiting example, the pump 40 may be configured to produce a flow rate of several mLs/min, which is significantly faster than the mLs/hour rates of prior microfluidic systems. In one specific embodiment the inlet and outlet channels 22, 23 may have a smallest effective dimension of 0.5 mm so that a 1 mL/min flow rate may generate a linear flow velocity of about 3 mm/sec in the channels and about 0.7 mm/sec through the reservoir 16. These linear velocities are nearly 100 fold lower than velocities believed to cause damage to target cells T. However, at this flow rate a typical 7.5 ml fluid sample may pass through the detector component 12 in 7.5 minutes or less. Similarly, a 3 mL/min flow rate would indicate a passage of a 7.5 mL sample in about 2.5 minutes.

The target cells and magnetic beads are under the influence of fluid flow that attempts to wash them away from the sensor chip surface as well as a magnetic force that attempts to draw them to the chip surface. The magnetic force produced by the magnet 32 can thus be calibrated to counteract the influence of the fluid flow F. In other words, a greater flow rate may be accomplished by increasing the magnetic force, since a greater force is required to dislodge the cells and beads from the fluid flow. A limiting factor to the strength of the magnetic field generated by the magnet 32 is that the magnetic force cannot be great enough to disassociate the magnetic beads B from the bound target cells T or great enough to damage the target cell as the beads are pulled by the magnetic force.

Figure 5C:
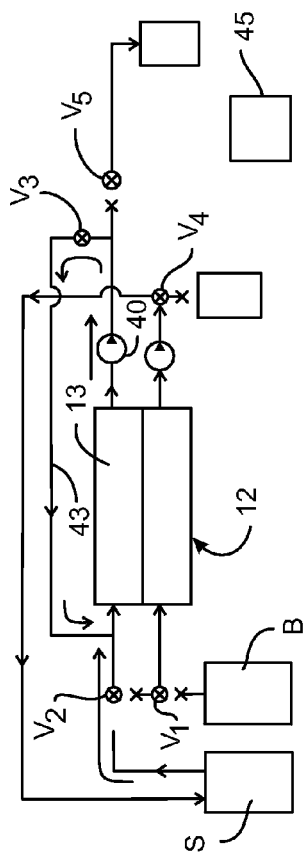

As the fluid sample flows through the first chamber 16a the magnet attracts the recognition elements M to the plate 18 and lower second reservoir 16b. As explained above, most of the unbound beads $M_B$ will pass through the openings 51 and into the lower reservoir 16b where they are held in place by the magnetic force. Likewise, the bound target cells T will be captured against the surface 51 of the apertured plate 18 so long as the magnetic force is present. The remaining sample fluid, less the captured target cells, may be delivered to the collection vessel CC. Alternatively, the valve V5 may be closed and the valve V3 opened to allow the sample fluid discharged from outlet 13b to be returned to the inlet 13a via bypass line 43, as reflected in the diagram of FIG. 5C. The use of the bypass can account for any bound target cells or any unbound magnetic beads that escape capture within the reservoir 16. The sample fluid may be continuously recirculated for a period of time deemed sufficient to capture all of the bound target cells.

It can be appreciated that at the end of the this second stage of the flow protocol all or at least a majority of the bound target cells T in the sample fluid have been captured against the surface 51 of the apertured plate 18 within the upper first chamber 16a. Likewise, all or at least a majority of the unbound magnetic beads $R_B$ have been pulled through the openings and are collected in the lower second chamber 16b. The captured target cells are thus available for viewing through the viewing panel 20 in order to count the number of target cells, for instance. It is contemplated that in a typical procedure the target cells will be rare or at an extremely low concentration within a sample (e.g., CTCs in a blood sample). Thus, the number of captured cells may be very low but easily discernible on the apertured plate. In one approach the captured cells may be viewed by bright-field microscopy. In addition, the captured cells may be further labeled with fluorescent reporters and visualized using fluorescent microscopy. Alternatively or in addition, the magnetic beads may be functionalized with a visual indicator, such as with fluorescent labeling. The magnetic beads may be visualized using fluorescence microscopy. Since the target cells are typically bound to a number of magnetic beads the fluorescent image of the beads will reveal the presence of the bound target cells. An example of captured target cells is shown in the bright-field microscopy image in FIG. 6. In this image the captured cells are clearly visible. The cells are MCF-7 (breast cancer cells) that are bound to magnetic beads functionalized with anti-EpCAM antibodies in a known manner. It can be noted that while the great majority of the several million unbound magnetic beads in the sample passed through the plate openings, some unbound magnetic beads are also present on the plate surface. However, it is apparent that the presence of these few beads does not interfere with a clear view of the captured target cells. In the specific example shown in FIG. 6 the openings have a diameter (or smallest effective dimension) of 5 μm and the magnetic beads have a diameter of 300 nm.

In order to improve visualization of the collected cells, the reservoir may be washed to eliminate the sample fluid and other cells that might visually interfere. In this instance, the magnetic field is maintained while the buffered solution from source B is flowed through the upper and lower portions of the reservoir. The washing cycle may be conducted in the same manner as the initially preparation cycle described above, namely by opening the two chambers 16a, 16b to the PBS solution, closing the valve V5 and opening the valve V4 to the buffer collection vessel BC. Since the magnet remains in position during this washing cycle the target cells will remain captured on the apertured plate within upper chamber 16a and the unbound magnetic beads will remain collected within the lower chamber 16b.

Figure 5D:
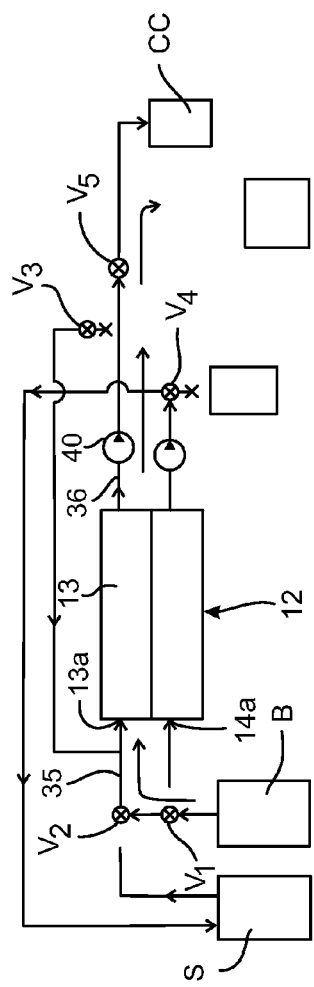

The microfluidic system 10 disclosed herein is also capable of collecting the captured target cells T as well as recovering the magnetic beads M. In one approach, the buffered solution (PBS) is flowed only through the upper first chamber 16a with the magnetic field removed. Thus, as shown in the diagram of FIG. 5D, the valve V1 is controlled to close flow to the inlet 14a but open to conduit 35 and valve V1. Valve V1 is controlled to prevent flow from the source S but accept the PBS flow from source B. Valves V3 and V4 are closed but valve V5 is open to the collection vessel CC. In the absence of the magnetic field the bound target cells are easily dislodged from the apertured plate. The flow of PBS can wash the target cells through the outlet conduit 23 and into a collection vessel CC. Since the second inlet 14a and outlet 14b are closed there is no fluid flow through the lower second chamber 16b. Thus, the collected beads M remain pooled at the bottom of the reservoir 16 even as the target cells are washed away. Alternatively, the magnetic field may be adjusted to reduce the magnetic force experienced by the bound target cells to a level sufficient to be overcome by fluid pressure from the PBS flowing through the upper chamber 16a. Since the pooled unbound beads in the lower chamber are closer to the magnet, the magnetic force is sufficient to hold the beads in place. Once the target cells have been removed and collected the magnetic field can be removed and valves V1 and V4 opened to flow PBS through the lower chamber to wash the unbound beads into the collection vessel BC. Alternatively, the valve V4 can be activated to open the bypass line 44 to redirect the unbound beads back to the sample source S. In this instance the unbound beads may be incubated to bind with any previously unbound target cells in the original source S or additional sources Si.

As previously described, the microfluidic system 10 may include additional detector components 12i that may be brought on line by via the valve V5. In certain protocols is may be contemplated that the sample fluid will flow continuously from the first detector component 12 to each successive detector component 12i before flowing to the collection vessel CC.

It is contemplated that the conduits and valves be formed of chemically inert materials. In a specific example the conduits 35, 36, 38, and 39, and the bypass lines 42-44 may be tubing such as 1/16 inch Cole-Parmer type tubes or other chemically-inert tubing. In certain procedures the source of target cells may be a conventional 7.5 mL whole blood sample in which the targeted cells have already been bound to recognition elements, such as magnetic beads. For a typical flow protocol, the buffer source B may be a 10 mL PBS reservoir or larger. In certain procedures the sample may be a processed blood sample in which the red blood cells have already been removed by means of lysing or by means of commercially available tubes, such as BD Vacutainer Cell Preparation Tubes. In other procedures the sample may be other bodily fluids such as urine, or may be water or other fluid samples collected from environmental or industrial sources.

In one embodiment the top and the bottom halves 15a, 15b of the detector component body 15 are machined out of acrylic and fastened by screws in a manner that sandwiches the apertured plate 18 and seal ring 29 to form a fluid tight seal between the chambers. However, other manufacturing and material are also envisioned, including but not limited to molded plastic formed in a plastic molding operation.

In one embodiment, the sensor chip apertured plate 18 is about a 15 mm by 15 mm silicon-on-insulator (SOI) wafer having a thickness of about 0.5 mm. The openings 50 may be limited to a predetermined active area of the detector component of about 10 mm by 10 mm. The array of openings (such as checker-board arrangement) may be defined on the wafer using lithography and then the holes formed by reactive ion etching of the front side of the wafer. Individual sensor chips may be defined by reactive ion etching of the back side of the wafer followed by HF etching of the insulating oxide. Alternatively, grooves may be defined using lithography and etched into the front side of a silicon wafer by reactive ion etching followed by coating with a thin layer of nitride. The nitride on the backside of the wafer can be patterned using lithography etched to define individual chips. Finally, the silicon wafer can be etched in the opening array pattern using reactive ion etching or potassium hydroxide, and the remaining nitride layer can be removed by etching. As discussed above, the openings have a smallest effective dimension that is sufficiently small to trap target cell-bound magnetic beads, yet sufficiently large to allow free magnetic beads that are not bound to the target cells to pass therethrough. In a specific example, the target cells are CTCs, so the openings need to be smaller than the targeted CTCs but larger than the beads. For example, the average size of a lymph node carcinoma of the prostate cells (LNCaP) or ovarian cancer cells (IGROV) is about 20 µm while the size of a certain type of magnetic bead may be about 1 µm. Hence, 3 µm openings will be large enough to easily pass a free bead but too small to let a CTC through. In a specific embodiment, the openings may be provided at about 30% packing density, which can result in about 14 openings underneath a 20 µm cell. Furthermore, if each cell is bound by multiple magnetic beads (as depicted in FIG. 4), each bead is pulled by the magnetic force so that the target cell is pulled down in multiple locations, making it even more difficult for a cell to pass through a single opening. The openings are also configured to trap the cell-bound magnetic beads to "lock" the target cells from moving horizontally, preventing them from being washed away from the surface of the plate by the fluid flow. In the embodiment illustrated in FIGS. 3-4, the openings 50 are shown as having a circular or cylindrical with a diameter. However, the openings may have other shapes, such as a conical bore or an oblong opening in the direction of the fluid flow F provided that the smallest effective dimension of the opening meets the dimensional requirements set forth above. In an alternative embodiment, the plate 18 may be configured with micro-grooves each having a width equal to the smallest effective dimension d discussed above sized so that the target cells cannot enter the micro-grooves but the much smaller magnetic beads can.

The apertured plate 18 may be coated or passivated with a physiologically inert material, such as bovine serum albumin (BSA) or poly ethylene glycol (PEG). Since the system according to the present disclosure does not utilize chemical binding between a functionalized target cell and the plate, the surface of the plate can be, and is preferably, non-reactive.

In accordance with the present disclosure, the target cell-to-magnetic bead binding is the only aimed affinity binding step, since the detector component 12 does not rely on chemically binding the target cells to a portion of the component. Magnetic beads are functionalized in many conventional ways, including with appropriate monoclonal or polyclonal antibodies (including but not limited to EpCAM antibodies), aptamers or short peptides that can bind to specific target cells. In an alternative functionalization strategy, low molecular weight ligands (e.g. 2-[3-(1,3-dicarboxy propyl)-ureido] pentanedioic acid or "DUPA" for prostate cancer cells, and folic acid for ovarian cancer cells or other cancer cells that over-express the folate receptor on their surfaces including lung, colon, renal and breast cancers) are used to promote binding to certain cells, most particularly CTCs. Specifically, low molecular weight ligands (e.g. DUPA and folate) can be produced with a functional group (amino, n-hydroxy succinamide (NHS), or biotin depending on the functional group on the magnetic bead to be used) with a PEG chain in between the low molecular weight ligand and the functional group to suppress nonspecific binding to the beads.

Functionalized beads are available from a variety of vendors with chemically reactive groups. Magnetic beads are also available in a wide range of sizes (from 100 nm to 5 µm, for example) that can be selected based on the dimensions of the target cell to which the beads are bound. In one embodiment NHS-coated 1 µm beads can be the starting point from Chemagen. For these beads, the PEG chain will be terminated with an amino group for covalent linkage to the NHS group on the bead. The beads can also be tested from other vendors with other functional groups, and can be terminated with the PEG chain and functional group accordingly. The beads can also be functionalized with fluorescent molecules using the appropriate chemistry for the functional group. For the example of a low molecular weight ligand, DUPA-PEG-amine and folate-PEG-amine molecules can be synthesized which can be reacted with the beads before fluorescent labeling. Thereafter, the desired amount of reactive fluorescent dye (fluorescein, for example) can be reacted with the beads, after which residual NHS groups (or other activated moieties on the beads) can be passivated by reaction with glucosamine (or another appropriate molecule for neutralizing the activated moiety on the beads). The ratio of folate-PEG-amine or DUPA-PEG-amine to fluorescent dye and passivating molecule can be optimized, as needed. Similarly, antibodies (such as the epithelial cell adhesion molecule or "EpCAM") can be immobilized on beads. One commercially available example, in which the functionalized magnetic beads are magnetic beads functionalized by attachment to a monoclonal antibody against the human Epithelial Cell Adhesion Molecule (EpCAM), such as Dynabeads® Epithelial Enrich, commercially available from Invitrogen. For example antibodies can be covalently linked to NHS-coated beads, or can be linked to streptavidin-coated beads via a biotin. Various other functionalization schemes can also be used including but not limited to carboxyl groups, thiols, and silanes. Alternatively, the beads may only have the recognition elements to bind and trap the cells on the plate surface but lack the fluorescent reporters which could be introduced separately to bind directly to the captured cells. In one procedure, fluorescently labeled antibodies (e.g. cytokeratin), low molecular weight ligands, peptides or aptamers can be separately exposed to the captured cells.

The microfluidic system 10 and detector component 12 disclosed herein are particularly suited to detection of cancer cells bound to magnetic beads. Many techniques are available for functionalizing and binding magnetic beads to target cells such as CTCs. Exemplary procedures are disclosed in the published the following publications: T. Mitrelias, et al., "Biological cell detection using ferromagnetic microbeads," *Journal of Magnetism and Magnetic Materials*, vol. 310, pp. 2862-2864, March 2007; N. Eide, et al., "Immunomagnetic detection of micrometastatic cells in bone marrow in uveal melanoma patients," *Acta Ophthalmologica*, vol. 87, pp. 830-836, December 2009; Yu et al., "Circulating tumor cells: approaches to isolation and characterization", The Journal of Cell Biology, Vol. 192, No. 3, pp. 373-382 (Feb. 7, 2011); Hayes & Smerage, "Circulating Tumor Cells", Progress in Molecular Biology and Translational Science, Vol. 95, 2010, pp. 95-112; Alexiou et al., "Medical Applications of Magnetic Nanoparticles", Journal of Nanoscience and Nanotechnology, Vol. 6, 2006, pp. 2762-2768; and Ito, et al., "Medical application of functionalized magnetic nanoparticles", Journal of Bioscience and Bioengineering, Vol. 100, 2005, pp. 1-11, the disclosure of each publication being incorporated herein by reference.

Publications disclosing exemplary procedures for synthesis and modification of folate and DUPA are identified in the Appendix. Any of the procedures and methods disclosed in these publications may be suitable for binding magnetic beads to select CTCs that may be subsequently captured by the detector component 12 disclosed herein. Functionalization of magnetic beads with folate is fully described in references listed in the Appendix, therefore one having ordinary skill in the art is enabled to functionalize similar magnetic beads with DUPA as further described in the listed references. The DUPA molecule itself is also fully described in references listed in the Appendix and elsewhere in this specification.

The ability to attract bead-bound cancer cells to a solid surface (i.e., without any openings) has been verified in experiments using MCF-7 cells (breast cancer cell line) attached to magnetic beads via EpCAM antibodies. The target cells were flowed with volumetric flow rates higher than 2 mL/minute and were successfully magnetically attracted to the solid surface during the flow. The target cells have a smallest effective dimension of about 20 μm so in another experiment the target cells were flowed over a plate having openings with an effective diameter of 5 μm. Intact cancer cells were observed on the plate using dual surface (cytokeratin) and nuclear (DAPI) staining. In these experiments 9 out of 10 target cells were detected in a 12 mL sample, for a 90% cell recovery.

The operation microfluidic detection system 10 disclosed herein can be controlled through a master controller 45. The controller may be a microprocessor configured to follow a controlled flow protocol according to a particular target cell, recognition element and sample size. The master controller may incorporate a reader to read indicia associated with a particular sample or samples, and automatically upload and execute a predetermined flow protocol associated with the particular sample.

The controller 45 may also be configured to allow user-controlled operation. For instance, the flow rate for a particular target cell-magnetic bead combination can be optimized by increasing the flow rate of a bound target cell sample until it is no longer possible to attract beads to the surface 51 of the apertured plate 18. The continuous operation of the system may be directly observed through the visualization window to determine whether a flow bypass is required or whether the detection process is complete.

In the illustrated embodiments the magnetic beads are described may be functionalized with a fluorescent marker. In these embodiments the apertured plate 18 is generally opaque so fluorescence signals coming from the unbound beads $M_B$ in the bottom chamber 16b will not be detected through the viewing panel 20. However, in cases some free beads may remain on the surface 51 and produce fluorescence signals that can confuse the visualization. In these cases the beads can be functionalized only with ligands and not with fluorescent markers. After the sample has been fully processed and the target cells captured on the apertured plate 18, fluorescent-tagged ligands may be introduced separately into the reservoir to bind to the target cells directly. The target cells can then be easily observed through the visualization panel 20. With this modified approach, in some cases the plate 18 can be devoid of any micro-apertures since the target cells on the plate surface can be readily differentiated from unbound magnetic beads by means of fluorescence.

In the detection process, the lower chamber 16b can be flooded with a minute amount of buffer or blood, after which here is no fluid flow through the lower chamber until the detection is complete. Fluid diffusion through the openings 50 between the upper and lower chambers 16a, 16b will be minimal since this microfluidic detection system 10 is not based on a pressure-driven flow.

CTCs from blood samples of patients of various cancers, including but not limited to prostate, ovarian breast, colon, renal and lung cancers, can be detected since many cancer cells express certain molecules or antigens on their surfaces which can be targeted with various recognition elements, including but not limited to antibodies (e.g., EpCAM), aptamers, low molecular weight ligands (e.g., folate and DUPA) and peptides. The beads can be functionalized as previously described (e.g., DUPA for prostate cancer cells, and folate end EpCAM for ovarian, breast, colon, renal and lung cancer cells) and then incubated and mixed with the sample fluid for 20-30 minutes. This incubation time may be longer or shorter depending on the number of beads used, sample volume and the number of target cells sought. For instance, seeding the sample with a larger number of beads increases the chance that a target cell will "find" a magnetic bead and bind. If there are multiple samples, incubation of all samples can be carried out simultaneously. The analysis of the sample fluid by the present detection system, and the sequence of sample fluid and buffer flows can be carried out as described herein. Aliquots of the captured cancer cells can be stained with additional recognition elements, such as antibodies to cytokeratins and EpCAM to assure that the cells retained by the detector component are indeed cancer cells. Furthermore, a preliminary indication of whether CTC numbers correlate with the stage of the disease of the sample donor can be ascertained. While the disclosed system is not limited to a particular type of cancer, prostate and ovarian cancer cells are especially mentioned herein as models for the system because both diseases can have vague symptoms resulting in confusing biomolecular tests, and both can benefit from a reliable, fast and sensitive CTC test. For example prostate cancer can have symptoms similar to benign prostatic hyperplasia. PSA biomarker tests can be confusing due to both false positives and false negatives. Similarly, ovarian cancer can have vague symptoms and may be detected as late as stage III or IV.

In comparison with a number of studies which successfully used magnetic beads to manually separate a wide variety of cells (from pathogens to T cells to CTCs) from complex samples, the approach according to the present disclosure advantageously offers separation-and-detection, faster analysis and the ability to harvest the captured cells and make them available for other types of analyses, including but not limited to genetic analysis. Furthermore, in comparison with giant magneto resistive (GMR) or spin-valve sensors which are known to a person of ordinary skill in the art (made of multiple nanolayers with precisely-controlled thicknesses) that can detect magnetic beads, the present approach advantageously is more robust, easy to construct and use, and offers much higher throughput. The system according to the present disclosure also offers a significant advantage over size-based cell entrapment assays which force the cells through micron-sized cavities by fluidic pressure. These assays can suffer from clogging of the cavities (since all entities in the sample are forced to pass through the cavities), or trapping of other entities similar in size to target cells, or complete passage and hence loss of target cells through the cavity.

The source S may include target cells that have already been bound to recognition elements, as well as magnetic beads. Alternatively the source may initially contain a sample fluid, such as a whole blood specimen, to which magnetic beads are added and allowed to incubate. Since the target cells are rare or at a low concentration, it is desirable to seed the specimen with millions of functionalized magnetic beads. For instance, in one approach 100 million beads are provided for each mL of whole blood specimen. A twenty minute incubation time has been found to be sufficient to bind rare CTCs. The system 10 may be primed as described above during the incubation period since the sample source S is not involved in the fluid flow during this step. Once the incubation period is complete the flow protocol for detecting the target cells described above may be implemented. Alternatively, as described above, the sample provided may be a blood sampled processed by a combination of commercial cell preparation tubes and centrifugation in order to discard red blood cells which are usually not sought during a CTC detection. Alternatively, the sample may be a processed blood sample wherein the red blood cells have been lysed using a red blood cell lysis buffer.

It is contemplated that the system 10 may be modified for incorporation into a dialysis or dialysis-type system. In this instance, functionalized magnetic beads may be injected into the patient's blood stream prior to dialysis. Rather than flowing into a collection vessel CC the blood flowing through the detector component 12 or detector components 12i is returned to the dialysis. A magnetic collection element may be incorporated at the system output to capture all unbound magnetic beads and bound cells that have not been collected within the detector component(s).

Those skilled in the art will recognize that numerous modifications can be made to the specific implementations described above. Therefore, above disclosure is not to be limited to the specific embodiments illustrated and described above. The description as presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others.

For instance, in the exemplary embodiments particular biological cells, such as CTCs, are described as being captured by the detector component 12 of the microfluidic detection system 10. Other entities, including particles or similar bodies, in the micrometer ($\mu$m) size range may also be detected and captured by the system disclosed herein, provided the particles or bodies can bind to one or more recognition elements, such as the magnetic beads described herein.

Furthermore, the apertured plate 18 is depicted as being generally parallel with the lower half 15b of the detector component base 15. Alternatively the plate may be angled toward the outlet channel 23 so that captured target cells tend to accumulate from the outlet end and fill in toward the inlet end. An angled plate may also facilitate passage of the unbound magnetic beads into the lower chamber 16b by inducing a translation along the surface 51 of the plate. Moreover, the plate 18 is shown as generally planar, although other configurations are contemplated that facilitate capturing target cells and passage of unbound beads.

The magnet 32 is described herein as a permanent magnet with the application of the magnetic field controlled by moving the magnet. The magnetic field may be manipulated by an adjustable shield disposed between the magnet and the reservoir 16. The shield may be used to completely block the magnetic field or to reduce the field as necessary. Alternatively the magnet may be an electromagnet that can be controlled by the controller 45 to activate or de-active the magnetic field or adjust the strength of the field. The controller may also modulate the magnetic field during a detection cycle to facilitate capturing the target cells and drawing the unbound magnetic beads into the lower chamber.

In a further alternative the magnet 32 may include multiple magnets arranged in a predetermined pattern to facilitate counting cells captured on the apertured plate 18. Thus, in one embodiment several magnets may be arranged in parallel strips so that the captured cells appear in several lines.

In the fluid flow protocols described above, the target cells are flushed from the detector component 12 in one step. Alternatively the cells may be retained on the apertured plate and the plate itself removed from the detector component. In this alternative the magnetic can remain in position as the upper body half 15a is removed to provide access to the apertured plate. The lower body half 15b may be transported with the apertured plate and magnet intact and mated with another body half for further procedures.

APPENDIX

References Pertaining to Synthesis of Folate Conjugates, Including Magnetic Particles and FITC Fluorescence Hapten 1. Kularatne & Low, "Targeting of Nanoparticles: Folate Receptor", Methods in Molecular Biology, 2010, Vol. 624, pp. 249-265
2. Xia & Low, "Folate-Targeted Therapies for Cancer", Journal of Medicinal Chemistry, 2010, Vol. 53, pp. 6811-6824
3. Sonvico et al., "Folate-Conjugated Iron Oxide Nanoparticles for Solid Tumor Targeting as Potential Specific Magnetic Hyperthermia Mediators: Synthesis, Physicochemical Characterization, and in Vitro Experiments", Bioconjugate Chemistry, 2005, Vol. 16, pp. 1181-1188
4. Lu & Low, "Folate targeting of haptens to cancer cell surfaces mediates immunotherapy of syngeneic murine tumors", Cancer Immunology, Immunotherapy, 2002, Vol. 51, pp. 153-162
5. Kohler et al., "Methotrexate-Modified Superparamagnetic Nanoparticles and Their Intracellular Uptake into Human Cancer Cells" Langmuir, 2005, Vol. 21, pp. 8858-8864
6. Zhang et al., "On the chemical synthesis and drug delivery response of folate receptor-activated, polyethylene glycol-functionalized magnetite nanoparticles", Acta Biomaterialia, 2008, Vol. 4, pp. 40-48
7. Corato et al., "Multifunctional Nanobeads Based on Quantum Dots and Magnetic Nanoparticles: Synthesis and Cancer Cell Targeting and Sorting", ACS Nano, 2011, Vol. 5, pp. 1109-1121

References Pertaining to the Structure & Synthesis of DUPA and its Binding to Resin Beads and FITC Fluorescence Hapten 8. Thomas et al., "Ligand-Targeted Delivery of Small Interfering RNAs to Malignant Cells and Tissues", Annals of the New York Academy of Sciences, 2009, pp. 32-39
9. Kularatne et al., "Synthesis and Biological Analysis of Prostate-Specific Membrane Antigen-Targeted Anticancer Prodrugs", Journal of Medicinal Chemistry, 2010, Vol. 53, pp. 7767-7777
10. Kularatne et al., "Prostate-Specific Membrane Antigen Targeted Imaging and Therapy of Prostate Cancer Using a PSMA Inhibitor as a Homing Ligand", Molecular Pharmaceutics, 2009, Vol. 6, pp. 780-789
11. Kularatne et al., "Design, Synthesis, and Preclinical Evaluation of Prostate-Specific Membrane Antigen Targeted $^{99m}$Tc-Radioimaging Agents", Molecular Pharmaceutics, 2009, Vol. 6, pp. 790-800
12. He et al., "Quantitation of circulating tumor cells in blood samples from ovarian and prostate cancer patients using tumor-specific fluorescent ligands," Int. J. Cancer: 123, 1968-1973 (2008)
43

What is claimed is:

1. A microfluidic detection system for detection of target cells in a fluid, the system comprising:
   (a) a plurality of magnetic beads, wherein each of said magnetic beads comprises a binding group that is capable of binding specifically to the target cells when said magnetic beads are added to the fluid containing the target cells, and wherein each of said magnetic beads has a largest effective dimension that is smaller than a smallest effective dimension of the target cells; and
   (b) a detector component comprising:
      a body defining a reservoir;
      a plate disposed within said reservoir and separating said reservoir into a first chamber and a second chamber, wherein said plate defines a plurality of openings therethrough, each opening having an effective dimension that is larger than the largest effective dimension of said magnetic beads and smaller than the smallest effective dimension of the target cells;
      wherein said body comprises a first inlet to said first chamber and a first outlet from said first chamber; and
      wherein said first chamber has a smallest effective dimension of about 0.5 mm to enable a flow of fluid through said first chamber at a flow rate of at least 1 milliliter per minute; and
      a magnet disposed in a cavity in said body so that said second chamber and said plate are situated between said magnet and said first chamber, wherein said magnet exerts a specific magnetic force and is arranged at a specific distance from said plate to generate a magnetic force at a surface of said plate facing said first chamber sufficient (i) to attract unbound said magnetic beads in said first chamber to said second chamber through said openings and (ii) to attract and hold the target cells bound to said magnetic beads on said surface of said plate without being moved away from said surface of said plate by fluid flowing through said first chamber.

2. The microfluidic detection system of claim 1, wherein said detector component includes a viewing panel arranged to enable a view of said surface of said plate facing said first chamber.

3. The microfluidic detection system of claim 2, wherein said viewing panel is an optically transparent glass.

4. The microfluidic detection system of claim 1, wherein said body further comprises a first inlet channel extending from said first inlet to said first chamber.

5. The microfluidic detection system of claim 1, wherein said magnet is adjustably mounted within said cavity to vary the distance between said magnet and said plate.

6. The microfluidic detection system of claim 1, wherein said body of said reservoir includes a second inlet to said second chamber and a second outlet from said second chamber.

7. The microfluidic detection system of claim 6, further comprising a pump that includes:
   a pump inlet connected to said first outlet of said body by a first conduit; and
   a pump outlet connected by a second conduit to a first vessel for receiving fluid pumped through said first outlet.

8. The microfluidic detection system of claim 7, further comprising:
   a first controllable valve disposed between said first outlet and said second outlet and the inlet of said pump; and
   a separate second controllable valve disposed downstream of said outlet of said pump.

9. The microfluidic detection system of claim 1, further comprising:
   an outlet conduit connected to said first outlet and connectable to a fluid vessel for receiving fluid pumped through said first outlet;
   a bypass line disposed between said outlet conduit and said first inlet; and
   a controllable valve for directing fluid flowing through said first outlet to either the fluid vessel or said bypass line.

10. The microfluidic detection system of claim 1, wherein the surface of said plate within said first chamber is provided with a physiologically inert coating.

11. The microfluidic detection system of claim 1, wherein the plate is angled with respect to said first chamber and said second chamber to bias the target cells to accumulate at said first outlet of said body.

12. The microfluidic detection system of claim 1, wherein said detector component further comprises:

a recirculation path configured to allow recirculation of the fluid from said first outlet of said first chamber to said first inlet of said first chamber.

13. The microfluidic detection system of claim 1, wherein said magnet is configured to be removable from said cavity in said body to permit dislodgment of target cells held on said plate.

14. The microfluidic detection system of claim 1, wherein each magnetic bead has a largest effective dimension of about 100 nm to about 5.0 microns.

15. The microfluidic detection system of claim 1, wherein each of said openings in said plate has an effective dimension of about 3.0 to about 5.0 microns.

16. The microfluidic detection system of claim 15, wherein each of said magnetic beads has a largest effective dimension of about 300 nm to 1.0 microns.

17. The microfluidic detection system of claim 1, wherein said first chamber has a smallest effective dimension of about 1.0 mm.

18. The microfluidic detection system of claim 17, wherein said pump is configured to flow the fluid at a flow rate of between 1 mL/minute and 3 mL/minute.

19. The microfluidic detection system of claim 18, wherein said pump is further configured to flow the fluid at a linear flow velocity of between 0.7 mm/sec and 2.1 mm/sec.

20. The microfluidic detection system of claim 17, wherein said pump is further arranged and controlled to flow a non-reactive liquid through the first chamber to dislodge target cells held on said plate.

21. The microfluidic detection system of claim 1, further comprising a pump and one or more conduits arranged and controlled to flow the fluid containing the target cells and said magnetic beads from a sample source into said first inlet and through said first chamber at a flow rate of at least 1.0 ml/minute.

22. The microfluidic detection system of claim 1, further comprising
  a pump and one or more conduits arranged to enable the fluid containing the target cells and said magnetic beads to flow from a sample source into said first inlet and through said first chamber; and
  a control module configured to control the pump to flow the fluid through the chamber at a flow rate of at least 1.0 ml/minute.

23. The microfluidic detection system of claim 22, wherein the control module is programmed to follow a controlled flow protocol.

24. The microfluidic system of claim 1, wherein said body is formed of a transparent material in at least a location that enables a view of said surface of said plate facing said first chamber.

* * * * *

UNITED STATES PATENT AND TRADEMARK OFFICE
CERTIFICATE OF CORRECTION

PATENT NO. : 9,494,557 B2  
APPLICATION NO. : 14/001963  
DATED : November 15, 2016  
INVENTOR(S) : Cagri A. Savran et al.

Page 1 of 1

It is certified that error appears in the above-identified patent and that said Letters Patent is hereby corrected as shown below:

In the Claims

Column 20, Line 23, Claim 24, after "microfluidic" insert -- detection --.

Signed and Sealed this
Fourteenth Day of February, 2017

Michelle K. Lee
*Director of the United States Patent and Trademark Office*